(12) United States Patent
Langeveld et al.

(10) Patent No.: US 7,736,588 B2
(45) Date of Patent: Jun. 15, 2010

(54) APPARATUS AND METHOD FOR DETECTING UNDESIRED RESIDUES IN A SAMPLE

(75) Inventors: Pieter Cornelis Langeveld, Delft (NL); Karl Heinrich Van Hemert, Delft (NL); Johannes Hendrik Pieter Machiel Kerkhof, Rozenburg (NL); Jacobus Stark, Rotterdam (NL)

(73) Assignee: DSM IP Assets B.V., Heerlen (NL)

( * ) Notice: Subject to any disclaimer, the term of this patent is extended or adjusted under 35 U.S.C. 154(b) by 1501 days.

(21) Appl. No.: 10/492,899

(22) PCT Filed: Oct. 10, 2002

(86) PCT No.: PCT/EP02/11369

§ 371 (c)(1),
(2), (4) Date: Apr. 15, 2004

(87) PCT Pub. No.: WO03/033728

PCT Pub. Date: Apr. 24, 2003

(65) Prior Publication Data

US 2005/0014281 A1   Jan. 20, 2005

(30) Foreign Application Priority Data

Oct. 15, 2001 (EP) .................. 01203936
May 15, 2002 (EP) .................. 02100496

(51) Int. Cl.
  *G01N 33/02* (2006.01)
  *C12Q 1/18* (2006.01)
  *G01J 3/46* (2006.01)

(52) U.S. Cl. .......... 422/68.1; 422/61; 422/55; 436/164; 436/171; 435/29; 435/32; 435/252.5; 356/402; 356/408

(58) Field of Classification Search .............. None
See application file for complete search history.

(56) References Cited

U.S. PATENT DOCUMENTS

| 5,434,053 A | 7/1995 | Piasio .................. 435/79 |
| 5,494,805 A | 2/1996 | Van Rijn et al. ........... 435/32 |
| 5,671,735 A | 9/1997 | MacFarlane et al. ........ 128/633 |
| 7,462,464 B1 * | 12/2008 | Langeveld et al. ........... 435/32 |
| 2003/0032064 A1 * | 2/2003 | Soller et al. ............... 435/7.1 |
| 2006/0134725 A1 * | 6/2006 | Langeveld .................. 435/32 |

(Continued)

FOREIGN PATENT DOCUMENTS

CA  2056581  5/1993

(Continued)

*Primary Examiner*—P. Kathryn Wright
(74) *Attorney, Agent, or Firm*—Nixon & Vanderhye P.C.

(57) ABSTRACT

Detection arrangement and method for detecting presence of a residue in a sample include determining color values of the sample, associated with the L*a*b color model. A value of a composite parameter Z is calculated as follows: $A = w_L + w_a a + w_b b$ where $w_L$, $w_a$ and $w_b$ are weighting factors having a value depending on the residue and the sample. A determination is made whether or not the sample comprises more or less than a predetermined amount of the residue in dependence on the value of the composition parameter Z. In a preferred embodiment, the arrangement is used to detect antibiotic residues, e.g. penicillin-G, in food products, elg. Milk, or body fluids, e.g. blood, urine.

10 Claims, 10 Drawing Sheets

U.S. PATENT DOCUMENTS

| | | | |
|---|---|---|---|
| 2007/0092929 A1* | 4/2007 | Dekker et al. | 435/32 |
| 2008/0020420 A1* | 1/2008 | Langeveld et al. | 435/32 |
| 2008/0293093 A1* | 11/2008 | Dekker et al. | 435/32 |

FOREIGN PATENT DOCUMENTS

| | | |
|---|---|---|
| DE | 3613794 | 10/1987 |
| EP | 0 005 891 | 12/1979 |
| EP | 0 285 792 | 10/1988 |
| EP | 0 288 621 | 11/1988 |
| FR | 2 637 083 | 3/1990 |
| GB | A-1467439 | 3/1977 |
| JP | 01/006864 | 1/1989 |
| JP | 06/118000 | 4/1994 |
| JP | 10/073491 | 3/1998 |
| JP | 10/073534 | 3/1998 |
| WO | WO98/32004 | 7/1998 |
| WO | WO00/68670 | 11/2000 |

\* cited by examiner

APPARATUS AND METHOD FOR DETECTING UNDESIRED RESIDUES IN A SAMPLE

CROSS-REFERENCE TO RELATED APPLICATIONS

This application is the national phase of PCT application PCT/EP 02/11369 having an international filing date of 10 Oct. 2002, which claims priority from European applications 02100496.5, filed 15 May 2002, and 01203936.8, filed 15 Oct. 2001. The contents of these documents are incorporated herein by reference.

FIELD OF THE INVENTION

The present invention relates to a detection arrangement for detecting presence of a residue in a sample, comprising a processor, a memory, a display, and a scanner, said memory, said display and said scanner being arranged to communicate with said processor, said scanner being arranged to generate light signals, to send said light signals to said sample, to receive reflected light signals back from said sample, to convert said reflected light signals into color signals and to send said color signals to said processor, said processor being operated by instructions stored in said memory and being arranged to display at least one color value on said display in accordance with said color signal, said at least one color value being associated with L*a*b color model.

It is observed that the term "sample" is here to be understood in a broad sense. Preferably, it refers both to parts that are (were) fixed to a body of an animal, human being or other living organism (e.g. plants) and to loose parts like milk, blood, fluid from muscle tissue, honey and eggs. More examples will be given below.

PRIOR ART

The presence of certain residues, e.g. pesticides, antibiotics or hormones, in food and feed is a growing concern among consumers due to health-related problems and the increase of drug resistant bacteria. Antibiotics are not only applied as medication but also as antimicrobial growth promoting substances.

Antimicrobial residues might be present in e.g. body liquids, organs, muscle tissues, eggs and plant tissues, which are used for consumption. Antimicrobial residues might also be present in food products in which said animal products are added as an ingredient. Examples of food products are milk; meat of cow, pig, poultry and fish; seafood such as shrimps; liver; processed meat products such as sausages, ready to eat meals, baby food vegetables and fruit. Antimicrobial residues might also be present in body liquids or animal tissues, which are suitable for examination by for example food-inspection authorities or centralized laboratories. Examples are milk, blood, pre-urine obtained from the kidney, urine, fluid from muscle tissue and other organs.

It is well known that food products such as consumption meat, organs, milk, sea-food, animal body liquids and animal tissues may contain too high concentrations of antimicrobial residues. In most countries, such as the countries of the European Union, Canada and the United States, Maximum Residue Levels (MRL) are regulated by legislation.

Test methods to detect antimicrobial residues in food products such as microbial inhibition tests (e.g. agar diffusion tests) or methods making use of selective binders (e.g. antibodies or tracers) have been known for a long time. Examples of microbiological test methods have been described in GB-A-1467439, EP 0005891, DE 3613794, CA 2056581, EP 0285792, U.S. Pat. No. 5,434,053 and U.S. Pat. No. 5,494,805.

These descriptions deal with, for instance, ready-to-use tests that make use of a test microorganism. The test microorganism is mostly (but not necessarily) imbedded in an agar medium, which may contain an indicator, a buffer solution, nutrients and substances to change the sensitivity for certain antimicrobial compounds in a positive or negative way. The indicator may be a color indicator, which changes its color in case the microorganism grows.

Examples of suitable test organisms are strains of *Bacillus, Streptococcus* or *E. coli*. In general the principle of these tests is that when antibacterial compounds are present in a sample in a concentration sufficient to inhibit the growth of the test organism the color of an acid/base or redox indicator will remain the same, while when no inhibition occurs the growth of the test organism is accompanied by the formation of acid or reduced metabolites that will change the color of the indicator.

The test may also be based on use of detecting molecules such as enzymes, antibodies, and complex formers. The detecting molecules may be attached to a color containing or color-generating molecule. A recipient molecule with affinity for the detection molecule is attached to a device (for instance, test tube or test strip). Upon absence of the analyte the detecting molecule will bind to the recipient molecule and develop a color. Also, strips can be designed where the presence of the analyte will result in the development of a color.

In the presence of an analyte, binding at the recipient site will not take place. A capture molecule with affinity for the analyte may be present on another location on for instance the test strip. In the presence of the analyte, the analyte-detection molecule-color generating molecule will bind to the capture region and develop a color.

The development of color and the difference in intensities between the colors of the recipient site and the capture site will determine the test result.

Until now, both tests with test organism and indicator and the tests containing binding molecules were mostly read visually. However, visual readings make detection of antimicrobial residues in samples (e.g. some types of milk such as individual cow milk, liver, urine, kidney, meat juice, eggs, honey, feed) not easy to perform. The reading made by eye is limited by the performance of the human eye and has limitation for making objective readings. Other types of tests, known in i.e. medical applications, involve color-reading devices that require the establishment of calibration curves using several reference concentrations of the analyte to be detected that are laborious to perform and do not yield an easily readable positive or negative result based on a given threshold value, but rather supply information on a concentration or concentration range.

SUMMARY OF THE INVENTION

It is an object of the present invention to provide an arrangement to detect the presence of residues in samples, using a color measurement to indicate whether or not the amount of residues is above a certain predetermined threshold.

To that end, the present invention relates to an arrangement as referred to at the outset that is characterized in that the processor as operated by the instructions is arranged to calculate a value of a composite parameter Z in accordance with a following equation:

$$Z = \sum_{x=1}^{x=n} w_x \cdot x$$

where $w_x$ is a weighting factor having a value depending on the residue and the sample and x is a color value depending on the color model, and to determine whether or not the sample comprises more or less than a predetermined amount of the residue in dependence on the value of the composite parameter Z. When using the L*a*b color model, the value of composite parameter Z is expressed by the following equation:

$$Z = w_L \cdot L + w_a \cdot a + w_b b$$

where $W_L$, $w_a$, and $w_b$ are weighting factors having a value depending on said residue and said sample, and to determine whether or not said sample comprises more or less than a predetermined amount of said residue in dependence on said value of said composite parameter Z.

By combining two or more of the color components in the L*a*b* model in a predetermined manner that depends on the type of residue and the sample, a much more accurate detection is possible than in the prior art.

The invention also relates to a method as claimed in claim 9, a computer program product according to claim 10, and a data carrier according to claim 11.

BRIEF DESCRIPTION OF THE DRAWINGS

The invention will be explained with reference to some drawings. The drawings are not intended to limit the scope of protection of the present invention but only to illustrate the invention. The invention itself is only limited by the scope of the annexed claims.

DESCRIPTION OF THE PREFERRED EMBODIMENT

Figure 1:
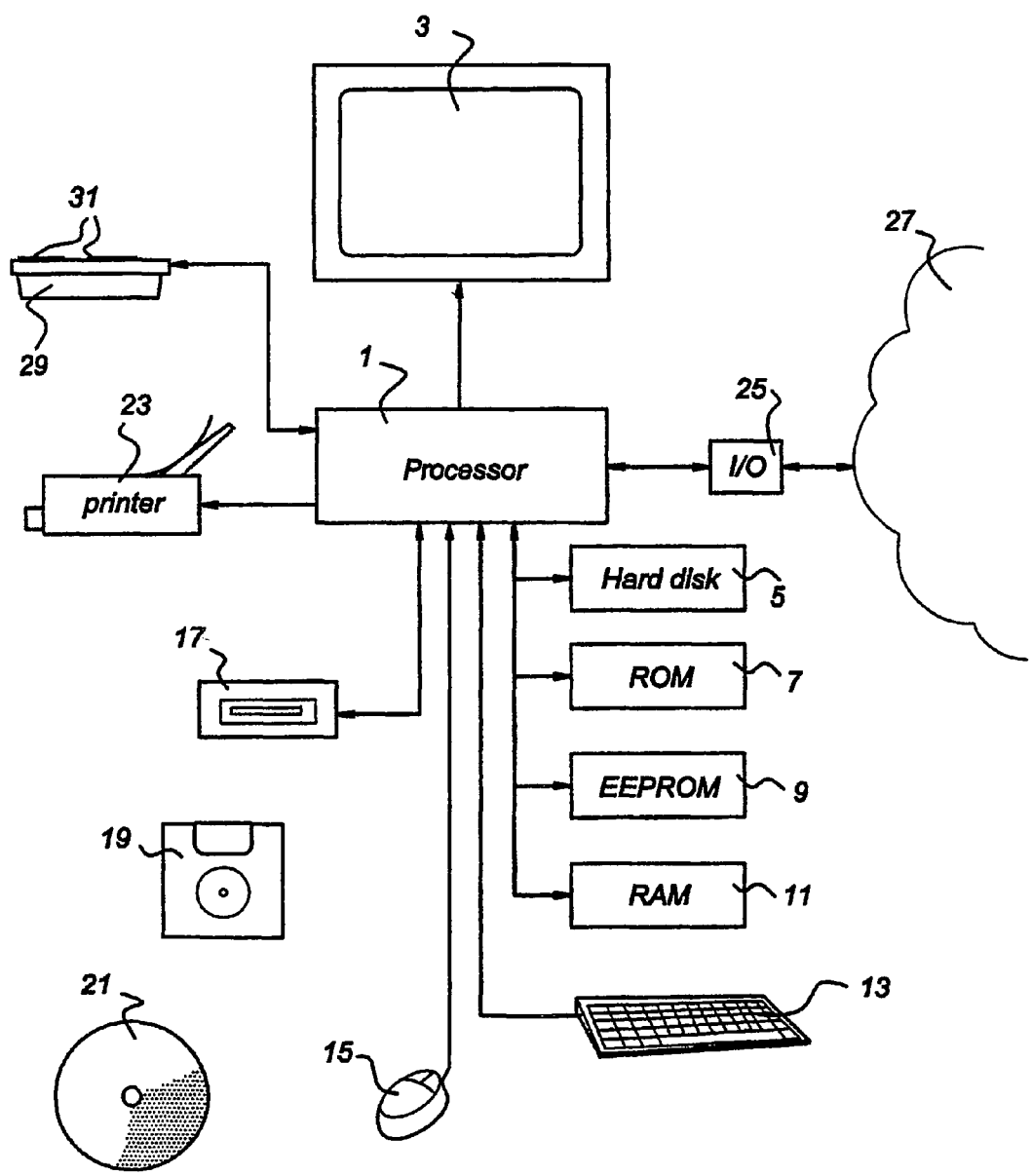
FIG. 1 shows a block diagram of the arrangement that can be used to carry out the present invention.

In FIG. 1, an overview is given of a detection arrangement that can be used to carry out the method according to the invention. The arrangement comprises a processor 1 for carrying out arithmetic operations.

The processor 1 is connected to a plurality of memory components, including a hard disk 5, Read Only Memory (ROM) 7, Electrically Erasable Programmable Read Only Memory (EEPROM) 9, and Random Access Memory (RAM) 11. Not all of these memory types need necessarily be provided. Moreover, these memory components need not be located physically close to the processor 1 but may be located remote from the processor 1.

The processor 1 is also connected to means for inputting instructions, data etc. by a user, like a keyboard 13, and a mouse 15. Other input means, such as a touch screen, a track ball and/or a voice converter, known to persons skilled in the art may be provided too.

A reading unit 17 connected to the processor 1 is provided. The reading unit 17 is arranged to read data from and possibly write data on a data carrier like a floppy disk 19 or a CDROM 21. Other data carriers may be tapes, DVD, etc, as is known to persons skilled in the art.

The processor 1 is also connected to a printer 23 for printing output data on paper, as well as to a display 3, for instance, a monitor or LCD (Liquid Crystal Display) screen, or any other type of display known to persons skilled in the art.

The processor 1 may be connected to a communication network 27, for instance, the Public Switched Telephone Network (PSTN), a Local Area Network (LAN), a Wide Area Network (WAN), etc. by means of I/O means 25. The processor 1 may be arranged to communicate with other communication arrangements through the network 27.

The processor 1 may be implemented as stand alone system, or as a plurality of parallel operating processors each arranged to carry out subtasks of a larger computer program, or as one or more main processors with several sub processors. Parts of the functionality of the invention may even be carried out by remote processors communicating with processor 1 through the network 27.

The processor 1 is also connected to a scanner 29, e.g., a HP 6300C Scanjet. On top of the scanner one or more test tube racks or microtiter plates 31 can be located. Instead of microtiter plates, other types of sample holding devices may be employed. Suitable examples are test tube racks containing test tubes designed in such a fashion that the contents are at least visible from the side with which they are placed on the scanner. Photographic images of said objects may also be placed on top of the scanner.

Alternatively, a device that can perform the same function as the scanner 29 may replace the scanner 29. Such a device may be a digital photo camera or video camera, a web cam apparatus or the like. Said devices may be arranged in such a manner that images from the object to be located can be conveniently collected. Preferably, the object is placed in a position above the lens of said device, for instance by using a mounting construction and/or a carrying area of transparent material such as a glass plate. The distance between the lens of said device and the object to be located is preferably less than one meter, more preferably less than 0.5 meter, most preferably less than 0.1 meter. Preferably a light source is installed in such a way that it will illuminate the object.

By carrying out certain functionalities by a central processor through a WAN such as the Internet, additional advantages can be realized. In this way, all users will use the same and the latest software versions, irrespective of their localization. Thus, the risk that in some cases outdated software is used, is circumvented. Drawbacks of using outdated software are e.g. the fact that the latest legislative requirements are not incorporated, corrections with regard to deviating scanners 29 or microtiter plates 31 are not incorporated, and results obtained by different users cannot be uniformly interpreted. Any person or organization, e.g. the manufacturer of the test systems or a regulatory institute, may operate the central processor. Thus, an additional advantage is that the manufacturer of the test systems or the regulatory institute can equip test systems with individual codes that are e.g. related to the production batch so that specifically tailored programs on the central processor can be accessed using the code. Preferably, access to said central processor is achieved using the Internet by means of personalized access code systems that are well known to the person skilled in the art. Alternatively, objects can be scanned or photographed by a user and the digital or analogous image resulting from this scan or photograph can then be send in various ways, i.e. by electronic mail, to the manufacturer of the test systems, a regulatory institute or others for further processing such as calibration, measurement or the like.

Figure 2A:
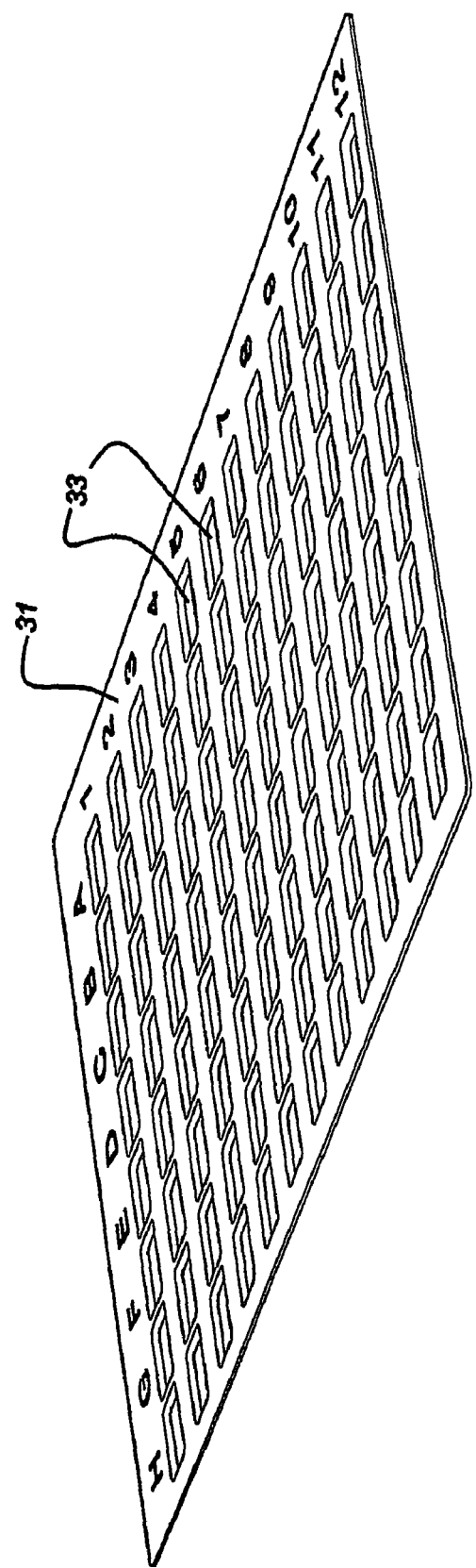
FIG. 2a shows a microtiter plate comprising a plurality of samples to be investigated.
Figure 2B:
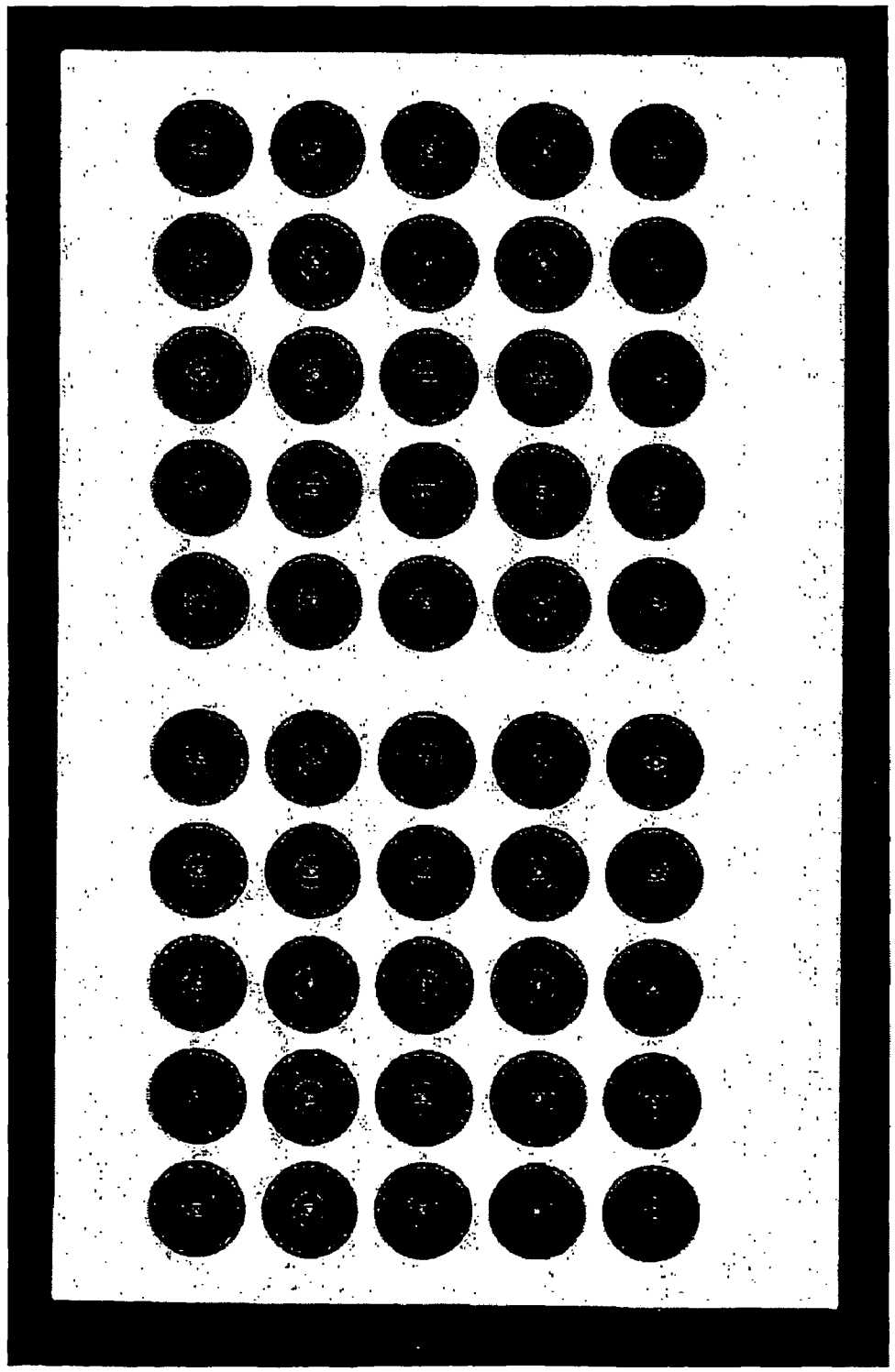
FIG. 2b shows a test tube rack comprising a plurality of samples to be investigated.

FIG. 2a shows a top view of an example of a microtiter plate 31 with 96 cups 33 to contain samples to be tested. FIG. 2b shows a bottom view of an example of a test tube rack 31 with 50 ampoules 33 to contain samples to be tested. The microtiter plate and test tube rack may be made of plastic or any other suitable material known to persons skilled in the art.

The invention will now be explained in detail with reference to some examples.

In a first embodiment (that is only intended as an example), the invention relates to detecting analytes, for example residues of antibiotics in milk. Nowadays, people use the Delvotest® to conduct such a test. Another example is the BR®-test. Delvotest® is a commercially available test set, which comprises an agar matrix, comprising residues of an acid forming microorganism, as well as a color indicator. First, a tablet with nutrients is applied on the test set and, than, 100 µl of the milk to be tested. This is followed by an incubation time of 2.5 hours with a temperature of 64° C. If there are no antibiotics (or only little) that inhibit the growth of the test organism, after a certain amount of time, an acid environment is formed by the growing microorganisms. Then, the color of the indicator changes from blue/purple to yellow. However, if there are sufficient antibiotics to inhibit that growth, the color of the indicator does not change and remains purple.

In a second embodiment, the invention relates to another suitable test for detecting antibiotic residues in meat, the Premi®Test. Premi®Test is a commercially available test set comprising an agar matrix, which comprises residues of an acid forming microorganism, nutrients, as well as a color indicator. First 100 µl of meat fluid to be tested is applied on the agar matrix. This is followed by a pre-incubation of 20 minutes at 20±3° C. After the pre-incubation the meat fluid is rinsed with water, preferably demineralized water, after which an additional incubation of approximately 3 hours at 64° C. is performed.

The embodiments described above are indirect detection methods. The word indirect in this respect refers to detection of a residue in a sample by means of visualization through one or more intermediate systems, i.e. a microorganism and/or a product formed by said microorganism and/or a color indicator displaying a color depending on the presence of said product. The person skilled in the art will understand that the method of the present invention is also suitably applicable for the direct detection of color components, for instance in recycle streams. The word direct in this respect refers to detection of a residue in a sample by means of measuring the color of the residue itself.

With the arrangement shown in FIG. 1 it is possible to automatically scan the bottom side of each of the test samples in the test plate. To that end, the scanner 29 produces light that is directed to the test samples in the test plate 31. Each of the test samples reflects the light received.

The scanner receives the reflected light and sends signals with color information of each of the scanned locations to the processor 1. The processor 1 stores the signals with color information in one of his memories, preferably, hard disk 5. This is all done automatically. Computer programs suitable to perform this function are available on the market, as is known to persons skilled in the art.

The color and the brightness of the reflected light are registered in three variables, each describing one color component with a color value. There are many different color models. However, most used color models are the RGB model (with a variable indicating the "amount" of anyone of the three colors red, green and blue, having color values R, G and B, respectively) and the so-called L*a*b* model. In the L*a*b* model, the color spectrum is divided in a two-dimensional matrix. The position of a color in this matrix is registered by means of the two color values "a" (x-axis) and "b" (y-axis). The color value L indicates the intensity (for instance, from light blue to dark-blue). It is preferred to use the L*a*b* model since this model is also used in color measurements of powders. It has been established that some of the color values L, a, and b display a larger contribution to the power of discernment of certain tests than others. For instance, when detecting residues of antibiotics in milk using the BR®-test or the Delvotest®, color value L can be omitted without significant loss in the power of discernment. Surprisingly, it has been established that this leads to improved test results when irregularities with the milk to be tested occur. Such irregularities may be the presence of milk below the test medium rather than above, the presence of milk outside the bottom of the test tube and the like. Likewise, when detecting residues of antibiotics in meat using Premi®Test, color value L may also be omitted.

The following procedure may be followed to obtain a very good color calibration. In order to let the measured (scanned) colors correspond with true colors, a scanner is to be calibrated. This can be done by scanning a reference object having known colors. Then, it is possible to determine a systematic deviation of an individual scanner and to correct colors in future scans. A suitable reference object is "Kodak Q-60 Color Input Target". This Q-60 target contains 264 colors of which the exact color values can be downloaded via Internet. The Q-60 targets are obtainable worldwide. Said calibration method affords a good and simple solution to the problem of conventional calibration procedures that involve the generation of a calibration curve using several reference concentrations of the analyte to be detected, for instance by using look-up tables, which are labor-intensive and do not in all cases provide decision values that correspond with those of traditional visual determinations. Furthermore, said calibration method will instruct each individual scanning device, in combination with the processor, to interpret any given color with the same numerical values as another scanning device. Yet another advantage of the calibration method according to the present invention, which is described in detail below, is that it can be performed only once for each individual scanning device. This can be performed at the location where the scanning device is to be used but also at other locations. By using the method as described below, calibration can be performed using a simple reference object such as, for instance, said "Kodak Q-60 Color Input Target". The method allows for simple fixation of a single reference point below or above which the result of a measurement is referred to as negative or positive. For example, when testing for antibiotics such as penicillin-G in samples such as milk, said reference point can be set at 4 ppb of penicillin-G, but every other value that serves a required threshold can also be incorporated. The method of the present invention thus involves a method that affords a variable threshold rather than a predetermined threshold.

According to one embodiment of the invention an optimal $w_L$, $w_a$, and $w_b$ value can be determined such that the group means shows a maximal distance in relation to the chosen threshold value. Once these optimal values of weighting factors are determined with help of reference samples, these values can be maintained for future tests having the same threshold value. In general, $w_L$, $w_a$, and $w_b$ values are not identical and preferably $w_a$, and $w_b$ are between 0.1 and 0.9. By means of illustrating the above procedure, the determination of optimal $w_L$, $w_a$, and $w_b$ values for detecting penicillin-G in milk is given below. The person skilled in the art will understand that a similar procedure can be followed for other types of detections.

All the samples on the test plates 31 were provided with milk with different concentrations of penicillin-G. In a first test there were 8 test plates provided with 48 samples with 100 µl milk and 48 samples with milk containing 4 ppb penicillin-G. In a second test there were 4 test plates with 32 samples with milk only, 32 samples with milk containing 1.5 ppb penicillin-G and 32 samples with milk containing 2 ppb penicillin-G.

Figure 3A:
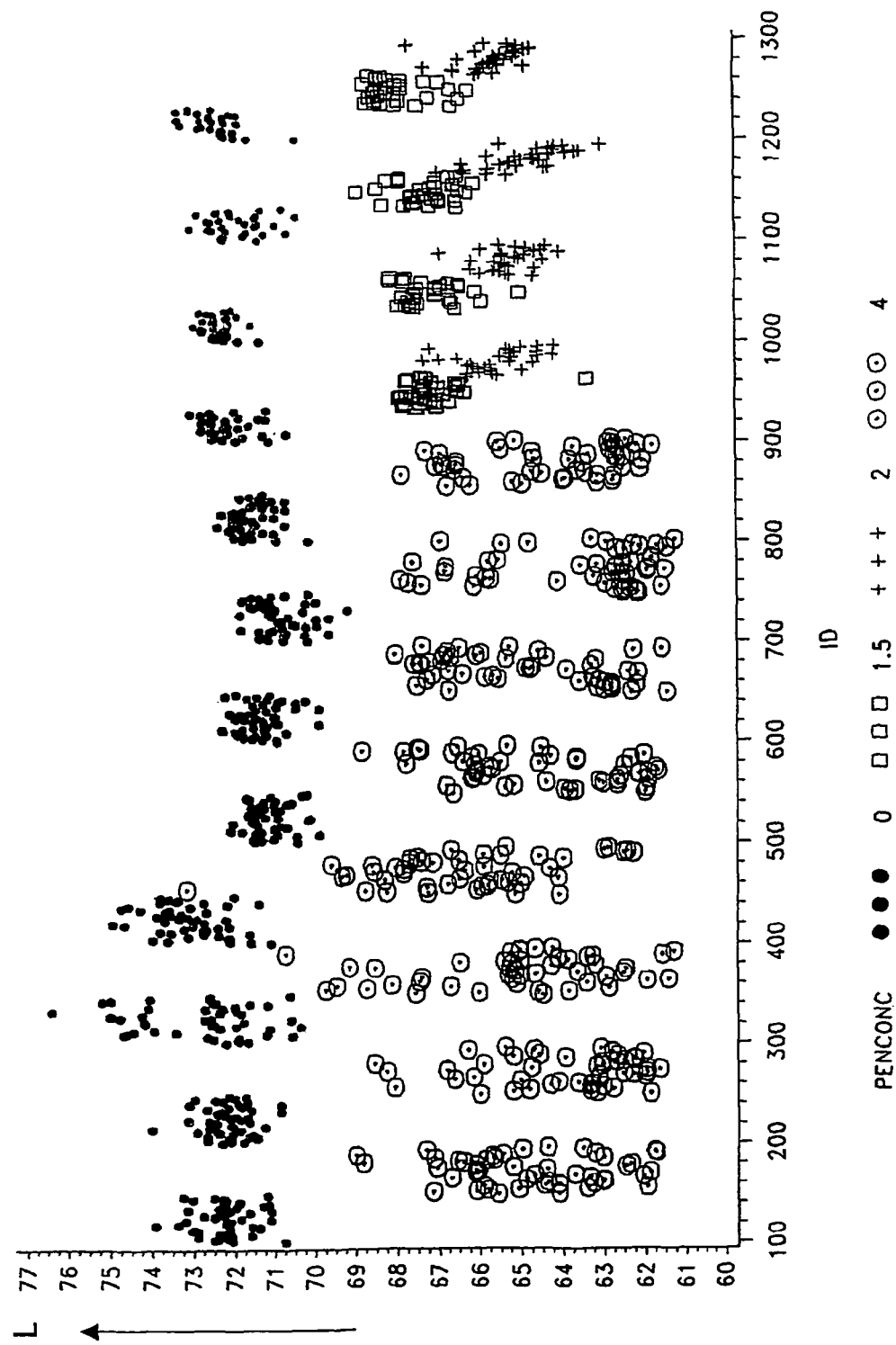
FIGS. 3a, 3b and 3c show test results for color values L, a, and b for different penicillin-G concentrations in milk, respectively.
Figure 3B:
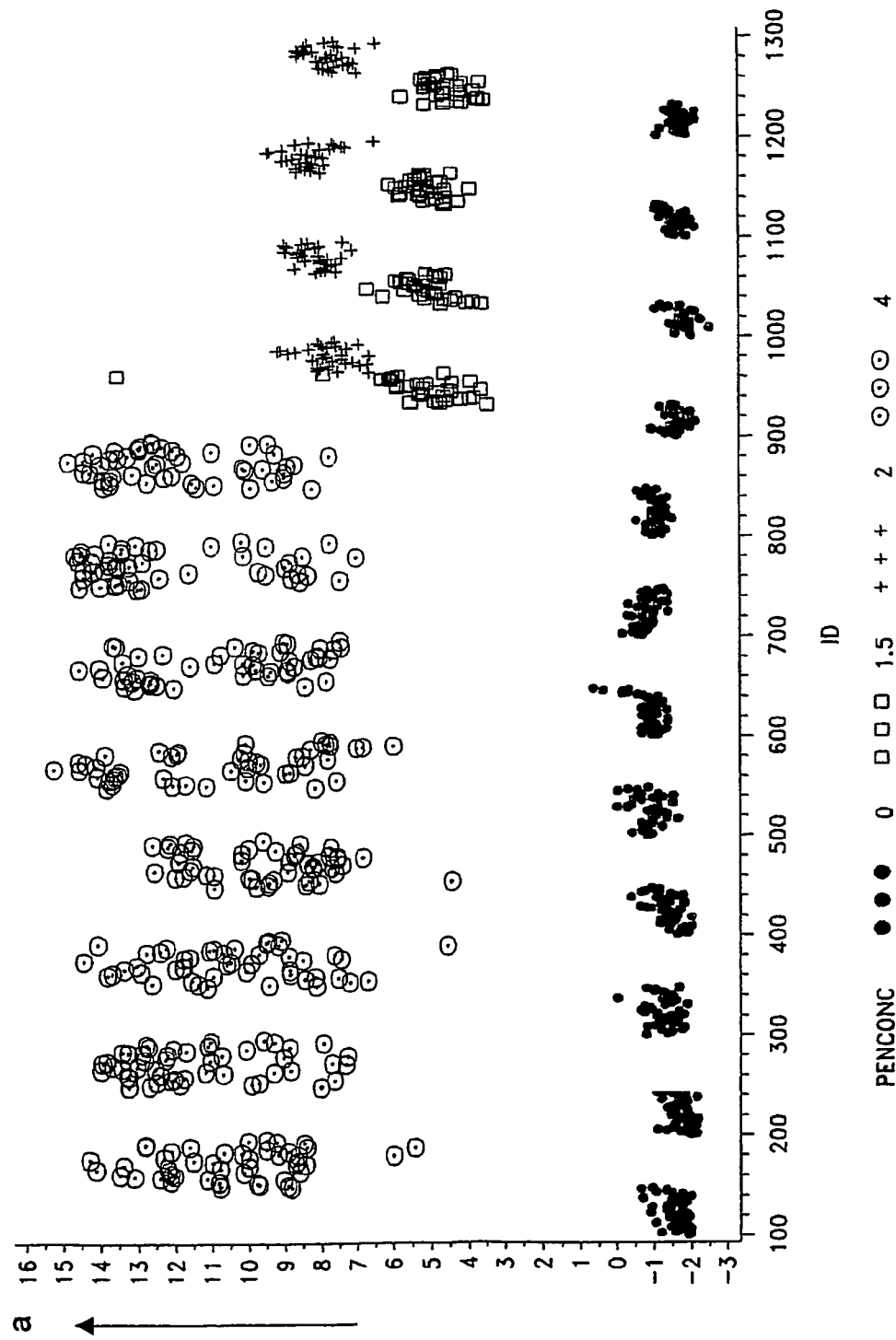
Figure 3C:
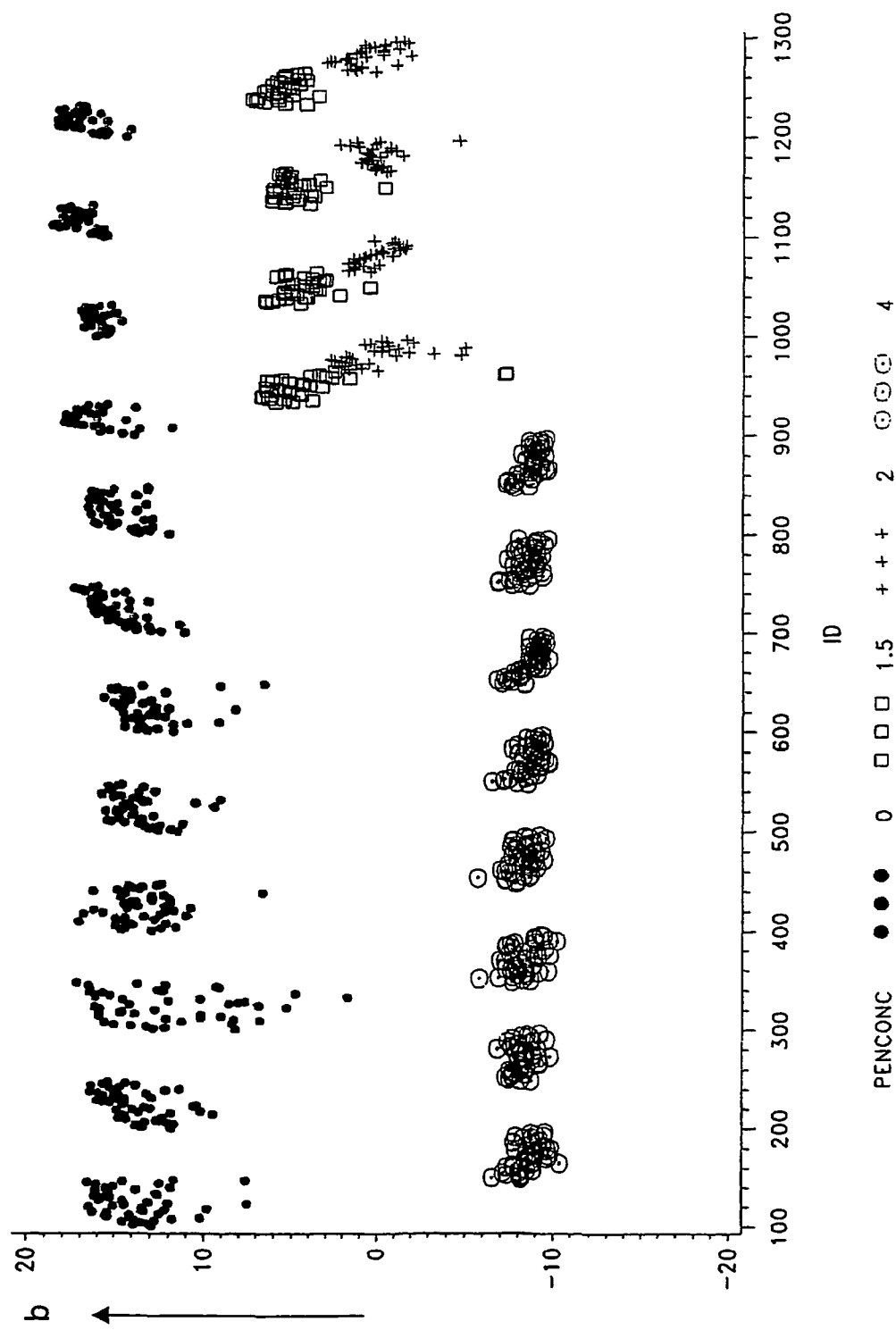

The L, a, and b color values as measured of these 12 plates, respectively are indicated in FIGS. 3a, 3b and 3c respectively. Every sample has a number: the last two digits refer to a cup (or sample) number on the plate concerned, whereas these last two numbers are preceded by one or two digits referring to the plate concerned. E.g., the 20$^{th}$ sample on the 11th plate has the number 1120. This number is on the x-axis, whereas the L, a, and b color values respectively are indicated on the y-axis.

In a first embodiment, the test method is intended to detect the presence of antibiotics in milk and not to provide a quantitative measurement of the concentration of antibiotics. In other words, the test must classify each of the milk samples in either "negative" or "positive", based on the measurement. A "negative" or "positive" decision refers to an amount of antibiotics below a certain threshold value or above that threshold value, respectively.

FIGS. 3a, 3b and 3c show that the separation between the measurements of the concentrations 0 and 1.5 ppb is best for the a-values (FIG. 3b), less with b-values (FIG. 3c), and worst with L-values (FIG. 3a). However, these figures also show that the separation between 1.5-2 ppb at the one hand and 4 ppb at the other hand is much better with the b-value. Thus, it can be concluded that the color values have another resolution. Moreover, this resolution depends on the concentration of penicillin-G.

FIG. 3b also shows that one can define, for instance, a=3 as a threshold value. Based on the measurements, it is not to be expected that milk samples without antibiotics will have an a-value higher than this threshold. In other words, if one finds a sample with an a-value higher than 3, it is almost certain that there is a residue in the milk.

However, if one finds an a-value lower than 3, one cannot conclude that there is no residue at all in the milk sample tested. Then, the residue concentration might, e.g., well be 1 ppb. If one finds an a-value lower than 3, one can conclude that the concentration of penicillin-G is most probably lower than 1.5 ppb.

In order to further improve the measurement method, the color values were listed against each other. In other words, a correlation pattern between the color values was made. It turned out that the correlation was dependent on the concentration of the residue. For instance, the group means of the L- and the a-values are negatively correlated. However, within the group of 0 ppb, the L- and a-values are uncorrelated and show a more negative correlation with increasing concentration towards 4 ppb. L- and b-values are almost uncorrelated within the groups but positively correlated between the groups below 4 ppb. Group means of the b- and a-values are negatively correlated. Within the groups, the b- and a-values are only correlated at 1.5 ppb.

Consequently, one can conclude that the samples of the same residue concentrations show almost no color differences and that the differences between the measurement values will be mostly due to measurement noise.

FIG. 3b shows that the a-value allows a good separation between residue concentrations of 0 and 1.5 ppb or more. However, the a-value measurements of the groups containing residue concentrations of 2 and 4 ppb overlap strongly.

However, b-values show the opposite relationship. For the groups with residue concentrations between 2 and 4 ppb there is no overlap of the b-value measurement results whereas there is overlap for the groups having residue concentrations between 0 and 1.5 ppb.

Therefore, it is possible to make a criterion comprising both color values, i.e., both a-value and b-value. To be more general, it is possible to use the a-value, b-value and L-value to make a composite function. In general, this composite function could be as follows:

$$Z = w_L L + w_a a + w_b b$$

where $w_L$, $w_a$ and $w_b$ are weighting factors for the L-value, a-value and b-value, respectively. The values of these weighting factors can be calculated by means of "discriminent analysis", such that the group means show a maximum distance in relation to the spreading. The composite parameter Z is then calculated for optimal power of discernment.

For all data as shown in FIGS. 3a, 3b and 3c it turns out that the optimum function is:

$$Z = 0.35a - 0.65b.$$

Of course, this optimum function is related to residues of penicillin-G in milk. Other optimum functions will be found for other residues in other sample types. Actually, the optimum function may also differ for the amount of penicillin-G in milk to be detected. For instance, if one wishes to distinguish residue concentration of 0, 1.5 and 2 ppb from one another, the optimum function may be:

$$Z = 0.70a - 0.15b - 0.15L$$

Thus, by varying the weighting factors, the amount of overlapping between the residue concentrations as measured is influenced in a different way.

In a second embodiment of the invention, quantitative measurements are made: by means of an appropriate selection of the weighting factor $w_L$, $w_a$, and $w_b$ it is possible to make a quantitative examination of residue concentrations in a certain range. For different residue concentration ranges, different values of the weighting factors will have to be selected.

Although the examples given below relate to penicillin-G in milk, enrofloxacin in meat, amoxicillin in chicken meat, and color components in recycle streams, it will be evident to a person skilled in the art that the method as explained is also applicable to β-lactam and quinolone antibiotics in general, but also to all other kinds of residue concentration measurements in samples, as referred to in the introduction of this description.

Thus, it has been shown that reliable and very simple to carry out, low cost scanning technology from consumer electronics can be used to improve current visual readings of diagnostic tests. Automatic reflection color analysis can be carried out very fast and improves significantly the assay performance in accuracy and the objectivity of test results.

The invention is not limited to using light of a visible spectrum. It is emphasized that the arrangement will also give good results using infrared or ultraviolet.

EXAMPLES

Example 1

Figure 4:
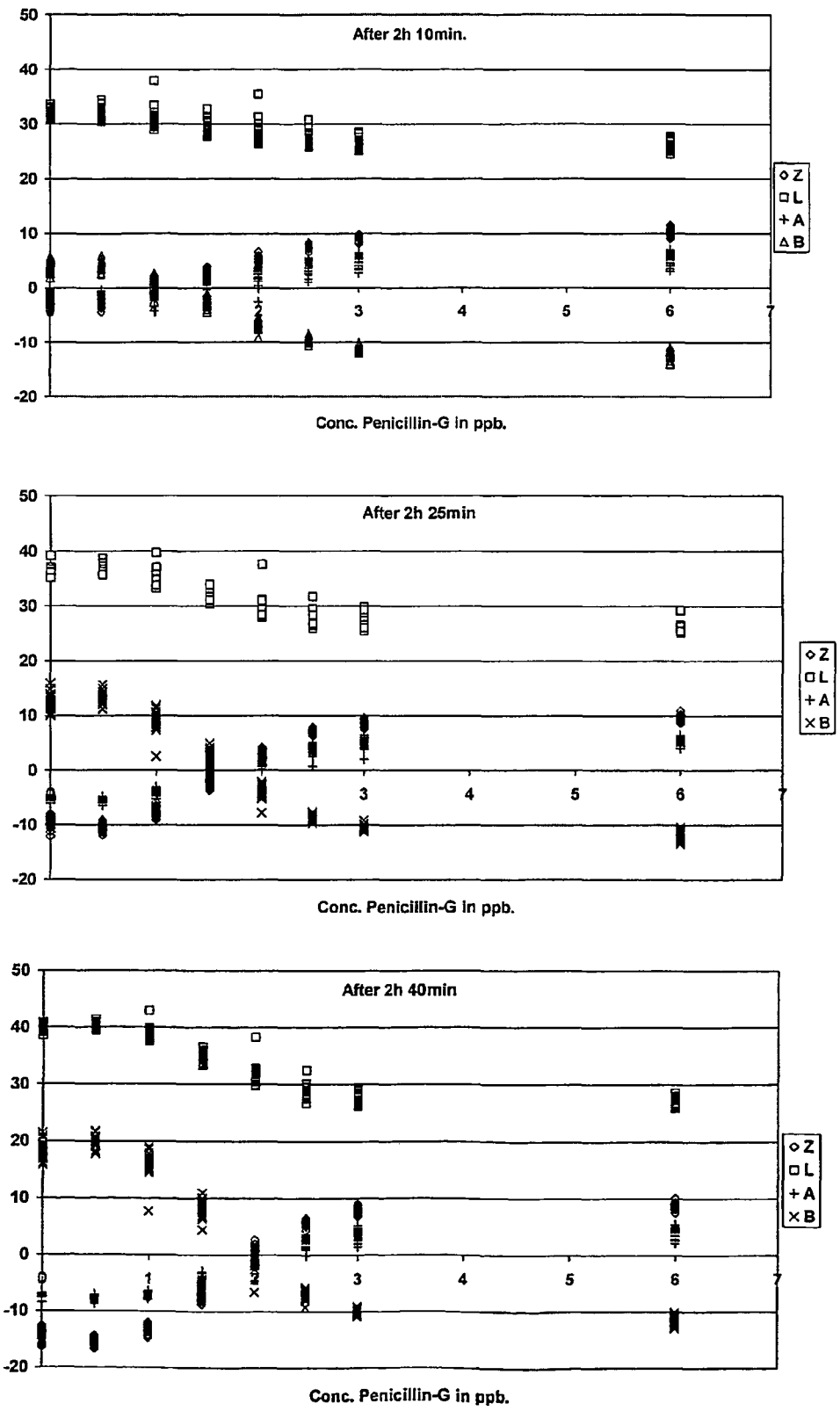
FIG. 4 shows test results for color values L, a, and b and composite parameter Z for different penicillin-G concentrations in milk at three different time intervals.

The samples on plate 31 were provided with milk with different concentrations of penicillin-G, 0 ppb, 0.5 ppb, 1.0 ppb, 1.5 ppb, 2.0 ppb, 2.5 ppb, 3.0 ppb, and 6.0 ppb, respectively. The L, a, b, and Z-color values as measured on these plates at three different time intervals are displayed in FIG. 4.

Example 2

Figure 5:
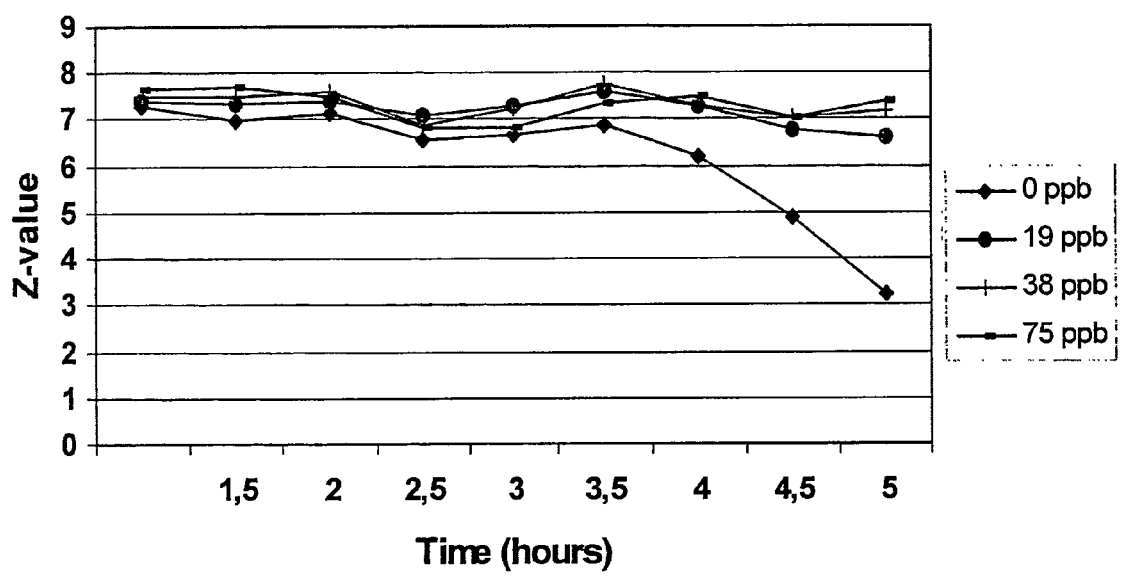
FIG. 5 shows test results for composite parameter Z for different enrofloxacin concentrations in meat fluid.

The samples on plate 31 were provided with meat tissue fluid with different concentrations of enrofloxacin, 0 ppb, 19 ppb, 38 ppb, and 75 ppb, respectively. In this example, the microorganism used is *E. coli*. The Z-color values as measured on these plates are displayed in FIG. 5. The Z-color values (y-axis) are measured during the time of the incubation (x-axis). The test method is designed to detect the presence of antibiotics. In other words, the test must classify each of the meat fluid samples in either "negative" or "positive" based on the amount of antibiotics below or above a certain threshold value, respectively. FIG. 5 shows that the separation between the measurements of the enrofloxacin concentrations 0 ppb, 19 ppb, 38 ppb, and 75 ppb increases with time.

Example 3

Figure 6:
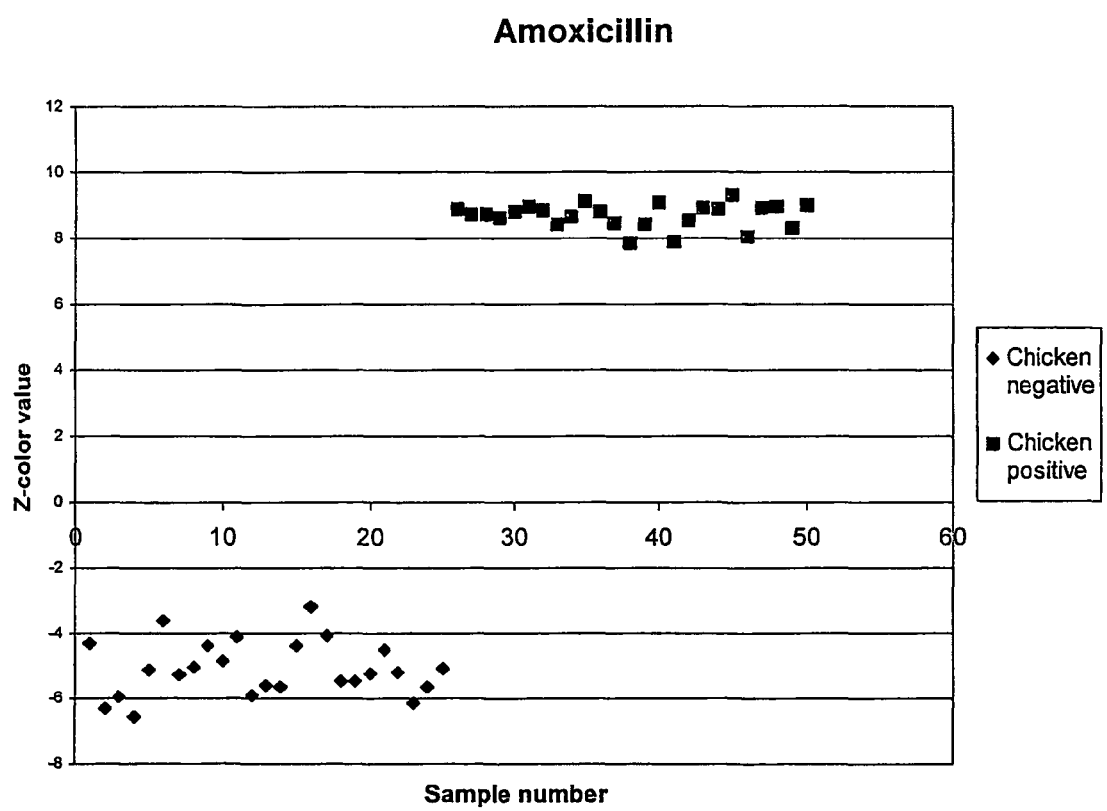
FIG. 6 shows test results for composite parameter Z for different amoxicillin concentrations in chicken meat fluid.

The samples on plate 31 were provided with chicken meat fluid with different concentrations of amoxicillin. 25 Ampoules were provided with 100 μl chicken meat fluid and 25 ampoules were provided with chicken meat fluid containing 10 ppb amoxicillin. The Z-color values as measured on this plate, are indicated in FIG. 6. The Z-color values (y-axis) are measured after an incubation time of 2 h50. Every sample is numbered and displayed on the x-axis. FIG. 6 shows the separation between the measurements of "negative" chicken meat fluid and "positive" chicken meat fluid (containing 10 ppb amoxicillin).

Example 4

This example relates to the detection of colored contaminants in recycle streams. In the production of antibiotic intermediates by-products can be formed which are of economic interest for process optimization. For example, a reactant can be recovered and recycled back to the process, reducing the raw materials cost. However, recycling of a target reactant may generate a build-up of undesired impurities such as color components. Not only should these components be reduced during the recovery of the target reactant, additional color generation should be avoided during subsequent processing steps such as, for instance, sterilization. Hence, color after sterilization becomes a specification for the recycle stream and should be measured. In this case, the method of the present invention is useful since it generates a quantitative measurement of the color, defined by L, a, and b color values. In the recycling of a reactant in a glucose-based fermentation process, a sterilization or heat shock is carried out by mixing a glucose solution with a fresh reactant solution in ratios that vary between 20/80 and 80/20. The mixture is heated up to 128° C. in a continuous system, with a residence time between 2 and 10 minutes.

Figure 7:
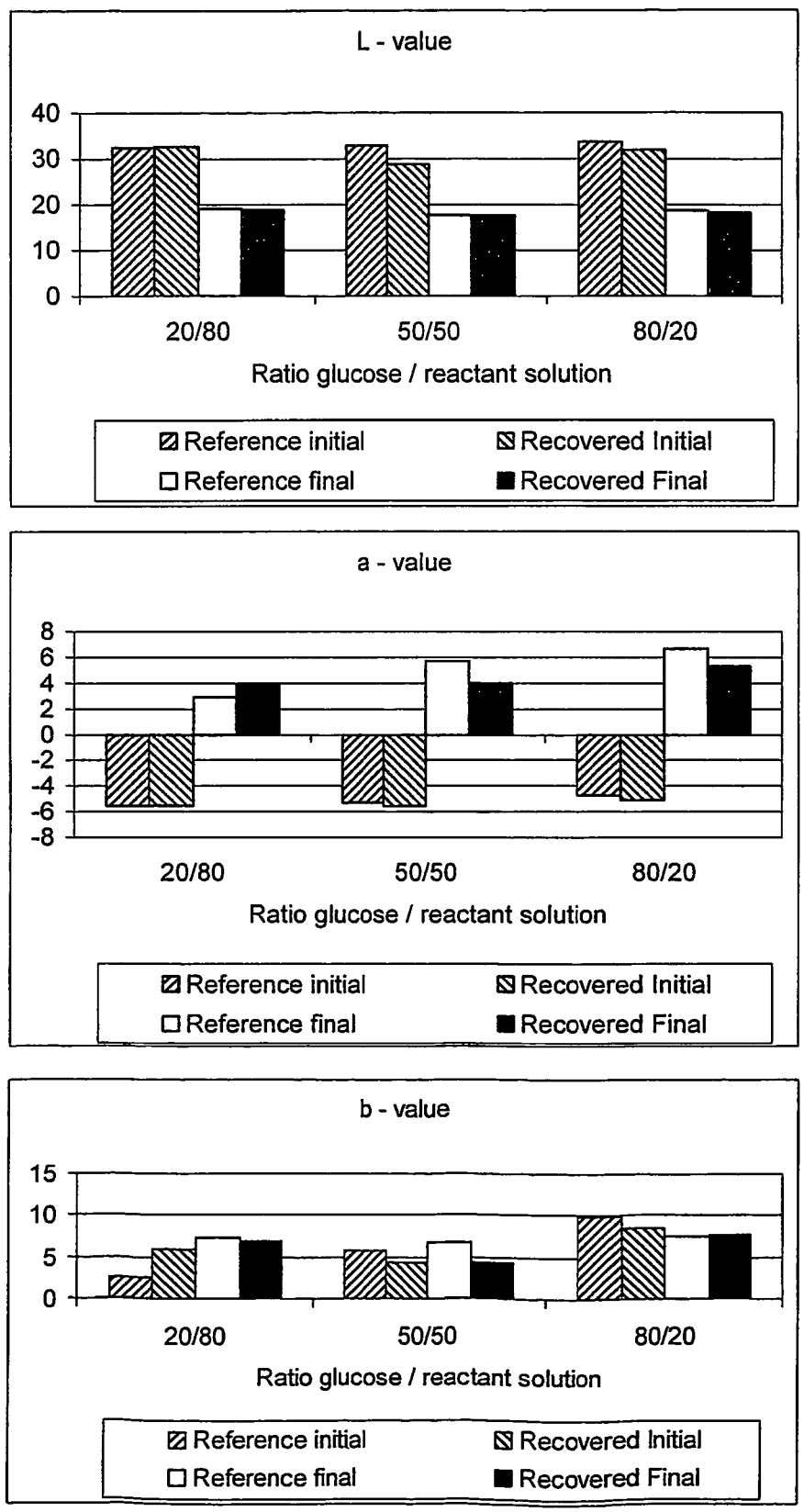
FIG. 7 shows test results for color values L, a, and b for concentrations of color components in recycle streams.

On a smaller scale, the heat shock can be carried out batch wise, in an autoclave, as follows. With the recovered reactant, and depending on its composition, a reactant solution with the same final composition as a fresh reactant solution is prepared. At least three reference mixtures with glucose solution and fresh reactant solution are prepared at ratios 20/80, 50/50 and 80/20. Three mixtures with glucose solution and recovered reactant solution at the same ratios as the reference mixtures are prepared. After thorough agitation, the initial color is measured according to the method of the present invention, at least twice per mixture. All the mixtures are placed in the autoclave at 128° C. during 10 minutes and the final color is measured according to the method of the present invention, at least twice per mixture. For a reactant recovered by crystallization and recycled as 40% of the total reactant required, the L, a, and b values before and after heat shock are presented in FIG. 7.

The invention claimed is:

1. A detection arrangement for detecting presence of a residue in a sample in relation to a threshold value of a selected composite parameter Z, wherein the detection arrangement comprises:
   a processor,
   a memory,
   a display, and
   a scanner,
   said memory, said display and said scanner being arranged to communicate with said processor,
   said scanner being arranged to generate light signals, to send said light signals to said sample, to receive reflected light signals back from said sample, to convert said reflected light signals into color signals and to send said color signals to said processor,
   said processor being operated by instructions stored in said memory and being arranged to display at least one color value on said display in accordance with said color signal, said at least one color value being associated with an L*a*b color model, wherein said processor calculates a value of a composite parameter Z in response to said instructions in accordance with a following equation:

$$Z = w_L \cdot L + w_a \cdot a + w_b \cdot b$$

wherein $w_L$, $w_a$, and $w_b$, are weighting factors indicative of residue concentration in a selected range, wherein $w_L$, $w_a$, and $w_b$, are not identical to one another and $w_a$, and $w_b$, are between 0.1 and 0.9, and wherein the weighting factors $w_L$, $w_a$, and $w_b$, are calculated by discriminate analysis and the composite parameter Z is calculated for optimal power of discernment, and wherein
   said processor determines whether or not the calculated composite parameter Z is more or less than the threshold value of the selected composite parameter Z to thereby determine the presence or absence, respectively, of the residue in the sample, and wherein
   said processor as operated by said instructions, calculates at least an absolute or a relative quantity of said residue in the selected range in said sample in dependence on said value of said calculated composite parameter Z.

2. The detection arrangement of claim 1, wherein said processor is connected to at least one remote processor through a network.

3. The detection arrangement of claim 1, wherein said sample is a body liquid, an animal tissue or a food product.

4. The detection arrangement of claim 3, wherein said food product is selected from the group consisting of milk, eggs, cow meat, pig meat, poultry meat, fish meat, sea food, and a processed meat product.

5. The detection arrangement of claim 3, wherein said body liquid is urine or blood.

6. The detection arrangement of claim 1, wherein said residue is a pesticide or an antibiotic.

7. The detection arrangement of claim 1, wherein said sample is milk, said residue is an antibiotic and said equation is: $Z=0.35a-0.65b$.

8. The detection arrangement of claim 7, wherein said milk has a temperature of 64° C.

9. The detection arrangement of claim 1, wherein said scanner is calibrated with a reference object having known colors.

10. The detection arrangement of claim 7, wherein said antibiotic is penicillin-G.

* * * * *